(12) United States Patent
Pfeifer et al.

(10) Patent No.: US 8,509,878 B2
(45) Date of Patent: Aug. 13, 2013

(54) SURGICAL REFERENCING UNIT, SURGICAL INSTRUMENT AND SURGICAL NAVIGATION SYSTEM

(75) Inventors: Tobias Pfeifer, Boesingen (DE); Rainmond Toth, Wurmlingen (DE)

(73) Assignee: Aesculap AG, Tuttlingen (DE)

( * ) Notice: Subject to any disclaimer, the term of this patent is extended or adjusted under 35 U.S.C. 154(b) by 117 days.

(21) Appl. No.: 13/135,595

(22) Filed: Jul. 8, 2011

(65) Prior Publication Data

US 2012/0004534 A1 Jan. 5, 2012

Related U.S. Application Data

(63) Continuation of application No. PCT/EP2010/050301, filed on Jan. 12, 2010.

(30) Foreign Application Priority Data

Jan. 27, 2009 (DE) .......................... 10 2009 007 291

(51) Int. Cl.
*A61B 5/00* (2006.01)
(52) U.S. Cl.
USPC ............................. 600/424; 600/407; 600/426
(58) Field of Classification Search
USPC ......................................... 600/407, 424, 426
See application file for complete search history.

(56) References Cited

U.S. PATENT DOCUMENTS

| | | | |
|---|---|---|---|
| 2003/0225329 | A1 | 12/2003 | Rossner et al. |
| 2004/0167391 | A1* | 8/2004 | Solar et al. ..................... 600/411 |
| 2005/0113659 | A1 | 5/2005 | Pothier et al. |
| 2006/0100638 | A1 | 5/2006 | Sarin et al. |
| 2006/0149276 | A1 | 7/2006 | Grimm |
| 2006/0173264 | A1 | 8/2006 | Jansen |
| 2007/0016009 | A1 | 1/2007 | Lakin et al. |
| 2008/0010706 | A1 | 1/2008 | Moses et al. |

FOREIGN PATENT DOCUMENTS

| | | |
|---|---|---|
| EP | 1 498 688 | 1/2005 |
| WO | 02/01148 | 1/2002 |
| WO | 2006/012491 | 2/2006 |
| WO | 2008/104548 | 9/2008 |

* cited by examiner

*Primary Examiner* — Peter Luong
(74) *Attorney, Agent, or Firm* — Lipsitz & McAllister, LLC (57) ABSTRACT

To improve a surgical referencing unit for a surgical navigation system, with which a spatial position and/or orientation of the referencing unit is determinable, the referencing unit comprising a base body and at least one marker element arranged on the base body, and the spatial position of the marker element being determinable by the navigation system, so that the handling thereof is simplified and possible errors are eliminated during use thereof, it is proposed that the at least one marker element be movably mounted on the base body, that the referencing unit comprise a first interface device which is configured for engagement with a second interface device provided on a surgical instrument or an implant in a connected position, and that the at least one marker element be movable into a predefined marker element position in dependence upon the interacting first and second interface devices.

25 Claims, 4 Drawing Sheets

SURGICAL REFERENCING UNIT, SURGICAL INSTRUMENT AND SURGICAL NAVIGATION SYSTEM

CROSS-REFERENCE TO RELATED APPLICATIONS

This application is a continuation of international application number PCT/EP2010/050301 filed on Jan. 12, 2010 and claims the benefit of German application number 102009007291.8 filed on Jan. 27, 2009.

The present disclosure relates to the subject matter disclosed in international application number PCT/EP2010/050301 of Jan. 12, 2010 and German application number 102009007291.8 of Jan. 27, 2009, which are incorporated herein by reference in their entirety and for all purposes.

FIELD OF THE INVENTION

The invention relates to a surgical referencing unit for a surgical navigation system generally, and more specifically to a surgical referencing unit for a surgical navigation system with which a spatial position and/or orientation of the referencing unit is determinable, the referencing unit comprising a base body and at least one marker element arranged on the base body, and the spatial position of the marker element being determinable by the navigation system.

The invention further relates to a surgical instrument or implant with a surgical referencing unit for a surgical navigation system generally, and more specifically to a surgical instrument or implant with a surgical referencing unit for a surgical navigation system, with which navigation system a spatial position and/or orientation of the reference unit is determinable, the referencing unit comprising a base body and at least one marker element arranged on the base body, and the spatial position of the marker element being determinable by the navigation system.

The invention also relates to a surgical navigation system generally, and more specifically to a surgical navigation system with at least one referencing unit and with at least one detecting device for detecting the spatial position and/or orientation of the referencing unit, the referencing unit comprising a base body and at least one marker element arranged on the base body, and the spatial position of the marker element being determinable by the navigation system.

BACKGROUND OF THE INVENTION

Surgical referencing units of the kind described at the outset are described in US 2006/0173264 A1, WO 02/01148 A2 and EP 1 498 688 A1, for example. They are usually configured such that relative positions between the marker elements cannot be changed, particularly when a plurality of marker elements are provided. In other words, a geometry or marker element geometry prescribed by the marker elements of the referencing unit cannot be changed. Since the referencing units can normally be connected to different instruments or implants, before these are used a calibration of the respective instrument or implant must be carried out after connection to the referencing unit, in order to establish a definite allocation of the referencing unit to the respective instrument or implant and to transmit this information to the navigation system.

Such a procedure involves effort and is also subject to error, as an operator who does not correctly select the instrument or implant connected to the referencing unit will not obtain the desired measured values from the navigation system, namely a position and/or an orientation of the instrument or implant in space, which is usually an operating theater.

Therefore, it would be desirable to provide an improved surgical referencing unit, an improved surgical instrument and an improved surgical navigation system.

SUMMARY OF THE INVENTION

In accordance with a first aspect of the invention a surgical referencing unit is provided for a surgical navigation system with which at least one of a spatial position and orientation of the referencing unit is determinable. Said referencing unit comprises a base body and at least one marker element arranged on the base body. The spatial position of said marker element is determinable by the navigation system. The at least one marker element is movably mounted on the base body. The referencing unit comprises a first interface device which is configured to be brought into engagement with a second interface device provided on a surgical instrument or an implant in a connected position, and the at least one marker element is movable into a predefined marker element position in dependence upon the interacting first and second interface devices.

In accordance with a second aspect of the invention a surgical instrument is provided with a surgical referencing unit for a surgical navigation system, with which navigation system at least one of a spatial position and orientation of the reference unit is determinable. Said referencing unit comprises a base body and at least one marker element arranged on the base body. The spatial position of said marker element is determinable by the navigation system. The at least one marker element is movably mounted on the base body. The referencing unit comprises a first interface device which is configured to be brought into engagement with a second interface device provided on the surgical instrument in a connected position, and the at least one marker element is movable, in dependence upon the first and second interface devices interacting in the connected position, into a marker element position predefined by the second interface device.

In accordance with a third aspect of the invention a surgical navigation system comprises at least one referencing unit and at least one detecting device for detecting at least one of the spatial position and orientation of the referencing unit. Said referencing unit comprises a base body and at least one marker element arranged on the base body The spatial position of said marker element is determinable by the navigation system. The at least one marker element is movably mounted on the base body. The referencing unit comprises a first interface device which is configured for engagement with a second interface device provided on a surgical instrument or an implant in a connected position, and the at least one marker element is movable, in dependence upon the interacting first and second interface devices, into a predefined marker element position.

BRIEF DESCRIPTION OF THE DRAWINGS

The following description of preferred embodiments of the invention serves in conjunction with the drawings for a more detailed explanation.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a surgical referencing unit for a surgical navigation system with which at least one of a spatial position and orientation of the referencing unit is determinable, said referencing unit comprising a base body and at least one marker element arranged on the base body, the spatial position of said marker element being determinable by the navigation system, wherein the at least one marker element is movably mounted on the base body, the referencing unit comprises a first interface device which is configured to be brought into engagement with a second interface device provided on a surgical instrument or an implant in a connected position, and the at least one marker element is movable into a predefined marker element position in dependence upon the interacting first and second interface devices.

Such a referencing unit has the advantage over the known referencing units that predefined marker element positions of the at least one marker element can be automatically set with the special interface device. If a plurality of marker elements are provided, optional marker element configurations or geometries can all be set by the first interface device. These can be clearly allocated to an instrument, for example, or can be prescribed by it by means of the second interface device. This avoids a corresponding referencing or calibration of the instrument or implant connected to the referencing unit in accordance with the invention, as previously required, thereby also eliminating any errors. With the first interface device, a coding prescribed by the second interface device on the instrument or implant, for example, can thus be automatically transferred to the referencing unit, so that with the navigation system it is possible to automatically determine, on the one hand, the type of instrument or implant by evaluating relative positions of the marker elements of the referencing unit and, on the other hand, a position and/or orientation of the instrument or implant connected to the referencing unit or of special parts thereof, for example, an instrument tip or an implant shaft.

It is expedient if the referencing unit comprises at least two marker elements. Providing at least two marker elements allows a relative position between these to be changed and, in dependence upon this, a clear allocation to instruments or implants to be established.

It is particularly advantageous if the referencing unit comprises three, four, five or six marker elements. The larger the number of marker elements, the more accurate a determination of a position or orientation of the referencing unit by means of the navigation system will be. Three marker elements are preferably required for optimal determination of the positions and/or orientation of the referencing unit in the operating theater. The redundancy of the data determined can be increased by provision of additional marker elements. Furthermore, accuracy in determining the referencing unit or its orientation or position can be achieved by increasing the spacings between the marker elements.

The at least one marker element preferably takes the form of an active marker element. Using active marker elements has advantages particularly if there is an increased risk of soiling of the marker element.

It is expedient if the active marker element comprises a transmitting unit for transmitting electromagnetic radiation or ultrasound. In particular, when it is somewhat soiled, such a marker element can also transmit radiation in such a way that a position of the marker element is determinable by a navigation system.

The manufacturing costs of the referencing unit can be reduced if the at least one marker element takes the form of a passive marker element. In addition, no power supply device is required for a passive marker element.

In order that a spatial position of the passive marker element is easily and safely determinable with a navigation system, it is expedient if a surface of the passive marker element is a surface which reflects electromagnetic radiation or ultrasound. This can be an inside or an outside surface of the marker element.

In accordance with a preferred embodiment of the invention, provision may be made for the surgical referencing unit to comprise a first coupling device which is configured for coupling with a second correspondingly configured coupling device which is provided on a surgical instrument or an implant, for releasably connecting the base body to the instrument or the implant. Such a coupling device is particularly suitable for mechanically fixing, in particular, temporarily fixing, the referencing unit to an instrument or implant.

The first coupling device can be manufactured particularly easily if it comprises at least one first coupling projection and/or at least one first coupling recess, which are configured so as to correspond to at least one second coupling recess and/or at least one second coupling projection of the second coupling device. The at least one first coupling projection and/or the at least one first coupling recess can thus be easily connected with force and/or positive locking to corresponding parts of a second coupling device.

It is advantageous if the referencing unit comprises a resetting device for transferring the at least one marker element from a marker element position deflected out of an initial position, which the at least one marker element assumes when the first interface device is not coupled to a second interface device, back into the initial position. With the resetting device, it is, in particular, possible to transfer the referencing unit which is not coupled to a second interface device to a defined position, namely the initial position described. In particular, the initial position may be so selected that the referencing unit can be easily connected to a second interface device of an instrument or an implant.

The referencing unit can be easily held in a defined manner in the initial position if the resetting device comprises at least one resetting member which holds the at least one marker element biased in the initial position.

The at least one marker element is preferably movable out of the initial position against the action of the resetting device into a deflected marker element position. The resetting device thus also holds the at least one marker element biased in the deflected marker element position. In particular, when the referencing unit is subjected to impulses, the resetting device also enables the at least one marker element to be transferred back into the defined, deflected marker element position again.

In accordance with a preferred embodiment of the invention, provision may be made for the first interface device to comprise at least one interface member which is coupled to the at least one marker element and is movably mounted and arranged in such a way that as a result of an actuating force acting on the interface member, the at least one marker element is movable from the initial position which the at least one marker element assumes when the first interface device is not coupled to a second interface device into a deflected marker element position. The interface member can thus be used, in particular, as element for applying force, in order to transfer an actuating force onto the at least one marker element.

In a referencing unit comprising a plurality of marker elements, to enable individual actuation of each marker element, it is advantageous if each marker element has an interface member of its own associated with it. It is also conceivable for only a subset of the provided marker elements to have an interface member of its own associated with it.

The referencing unit is of particularly simple construction if the interface member is displaceably mounted on the first interface device. Optionally or alternatively, a pivotal arrangement is, of course, also conceivable.

It is advantageous if the interface member is deflectable from the initial position against the action of the resetting device into a deflected interface member position. This makes it possible for the interface member to be held biased in the deflected interface member position by the resetting device, and the at least one marker element coupled to the interface member can thereby also be held in a defined position.

To enable easy and safe actuation of the interface member, it is advantageous if it comprises an actuating section which, in the initial position, projects at least partially from the base body. The actuating section can, for example, also project from the base body in a depression formed thereon, so that the actuating section does not necessarily have to project, but may project, beyond an outer contour defined overall by the base body.

The construction of the referencing unit is simplified further if the base body comprises a base area and if, in the initial position, the actuating section projects beyond the base area. If, for example, the base area is of flat configuration, and the base body is placed; for example, on a flat surface area, the actuating section is then inevitably actuated and pushed into the base body until it no longer projects over its flat base area.

It is advantageous if an interface member guiding device is provided for guiding movement of the interface member from the initial position into a deflected interface member position and/or back. With the interface member guiding device, it is possible to guide movement of the interface member in a defined manner.

It is particularly easy to construct the interface member guiding device if it comprises a guide sleeve in which the interface member is movably guided, and if, in the initial position, an actuating section of the interface member projects at least partially beyond the guide sleeve. Optionally, the actuating section of the interface member can also be completely surrounded by the guide sleeve in the initial position. To actuate the interface member or its actuating section, a projection, for example, can then engage the guide sleeve in order to push the interface member further into the guide sleeve.

The interface member is preferably coupled to the at least one marker element by a force transmitting member. With the force transmitting member, it is possible to transfer an actuating force acting on the actuating section of the interface member onto the at least one marker element. In particular, the force transmitting member may take the form of a push-and-pull member for transferring push and/or pull forces from the interface member onto the at least one marker element.

At least two interface members of the referencing unit are advantageously movable independently of each other. All interface members of the referencing unit are preferably movable independently of one another. The more interface members are movable independently of one another, the more different, but defined marker element geometries can be prescribed with the referencing unit.

The present invention relates to a surgical instrument or implant with a surgical referencing unit for a surgical navigation system, with which navigation system at least one of a spatial position and orientation of the reference unit is determinable, said referencing unit comprising a base body and at least one marker element arranged on the base body, the spatial position of said marker element being determinable by the navigation system, wherein the at least one marker element is movably mounted on the base body, the referencing unit comprises a first interface device which is configured to be brought into engagement with a second interface device provided on the surgical instrument in a connected position, and the at least one marker element is movable, in dependence upon the first and second interface devices interacting in the connected position, into a marker element position predefined by the second interface device.

Such a surgical instrument or implant in accordance with the invention makes it possible, with one of the above-described standard referencing units in accordance with the invention, by virtue of the configuration, in particular, of the second interface device, which may comprise a coding for a marker element geometry, to allocate a definite marker element geometry to the instrument or implant so as to enable it to be clearly identified and its spatial position and/or orientation determined with the navigation system. If different instruments are equipped with different second interface devices, then owing to the interaction of the first and second interface devices in a connected position, a definite marker element geometry can be allocated, namely automatically, to each instrument or implant with only one type of referencing unit. Calibration or referencing of the instrument in order to manually allocate the referencing unit to the selected instrument and initially determine a spatial position and/or orientation of the referencing unit or the instrument is no longer required.

It is also advantageous if the referencing unit is one of the referencing units described above. The surgical instrument is then characterized by the advantages described above in conjunction with the special embodiments of the referencing units in accordance with the invention.

It is expedient if the second interface device comprises at least one coding element which, in interaction with the first interface device, forces the at least one marker element into the predefined marker element position. The at least one coding element therefore makes it possible to force the at least one marker element into a predefined marker element position. If the referencing unit has a plurality of marker elements, a marker element geometry can thus be specifically changed by means of the at least one coding element or by means of a plurality of coding elements of the second interface device so as to establish a definite allocation of the marker element geometry to the second interface device. The desired marker element geometry is therefore only prescribed upon interaction of the first and second interface devices and not during manufacture of the referencing unit. This makes it possible, in principle, to set any number of marker element geometries with only one basic type of referencing unit. The marker element geometries can, in turn, be easily coded by means of the second interface device. The referencing unit can therefore be coded by the instrument or the implant, thereby eliminating the need for initial or start referencing of the instrument, as it is already possible to automatically clearly determine the type of instrument or implant, for example, on the basis of the marker element geometry set during interaction of the two interface devices.

To enable selective use, as far as possible, of all conceivable marker element geometries that are prescribable with the referencing unit, it is expedient if the second interface device comprises at least as many coding elements as marker elements are provided on the referencing unit. In particular, a coding element may also be so configured that the at least one marker element is not deflected from its initial position if the first and second interface devices are in engagement with each other and are interacting.

It is advantageous if the at least one coding element takes the form of a projection or a recess with which an interface member comprised by the first interface device is engageable in the connected position. In this context, engageable means, in particular, also that the at least one coding element and the interface member only touch or lie against each other when they are interacting. Any other engagement with force and/or positive locking is not absolutely necessary, but optionally possible.

Marker element geometries can be set particularly easily if the marker element position is prescribable by a depth of the recess or a height of the projection. A marker element position can thus be easily and purely mechanically prescribed by the at least one coding element.

The construction of the second interface device is particularly simple if it comprises a second base body which carries the at least one coding element. A further base body of the second interface device, as well as a base body of the first interface device, is generally also to be understood as a support or a support unit for the at least one marker element or the at least one coding element.

Manufacture of the interface device is further simplified if the at least one coding element is immovably formed on the second interface device. The second interface device can thus be constructed, in particular, without any movable parts.

To enable easy connection of the instrument to the referencing unit, it is expedient if it comprises a second coupling device which is configured for coupling with a first correspondingly configured coupling device which is provided on the referencing unit, for releasable connection of the base body to the instrument or implant.

It is expedient if the second coupling device comprises at least one second coupling projection and/or at least one second coupling recess, which are configured so as to correspond to at least one first coupling recess and/or at least one first coupling projection of the first coupling device. In particular, a connection between the instrument or implant, on the one hand, and the referencing unit, on the other hand, with force and/or positive locking can thus be easily made in a coupled or connected position.

The present invention also relates to a surgical navigation system with at least one referencing unit and with at least one detecting device for detecting at least one of the spatial position and orientation of the referencing unit, said referencing unit comprising a base body and at least one marker element arranged on the base body, the spatial position of said marker element being determinable by the navigation system, wherein the at least one marker element is movably mounted on the base body, the referencing unit comprises a first interface device which is configured for engagement with a second interface device provided on a surgical instrument or an implant in a connected position, and the at least one marker element is movable, in dependence upon the interacting first and second interface devices, into a predefined marker element position.

Such a surgical navigation system facilitates the work in the operating theater as the special configuration of the instruments, implants and referencing units and the adapted functionality and design of the navigation system enable determination of a position and/or orientation of an instrument or implant, and, at the same time, and, in addition, also the type of implant or instrument, namely automatically, by means of the navigation system. This preferably comprises a database of all available instruments and implants with second interface devices and their codings, so that the instrument itself or at least its type, also in the case of the implants, can be automatically determined by the surgical navigation system from a certain spatial arrangement of the marker elements of the referencing unit after connection to the respective instrument or implant. As a result of the solution in accordance with the invention, a manual allocation of a certain marker element geometry of the referencing unit to an implant or an instrument is no longer required.

The surgical navigation system expediently comprises one or more of the surgical referencing units described above. The surgical navigation system as a whole then also has the advantages described in conjunction with the preferred embodiments of the referencing units.

It is also expedient if the surgical navigation system comprises one or more of the surgical instruments described above. In the same way, the surgical navigation system then has the advantages described in conjunction with the preferred embodiments of the instruments.

The surgical navigation system preferably comprises two or more instruments of the kind described above, which have different, coded second interface devices for different positioning of the at least one marker element of the referencing unit. If such instruments are connected to one of the referencing units described above, a geometry of the marker elements, i.e., in particular, their positions relative to one another, is changed in a specific manner so that the navigation system can automatically identify the instrument or implant connected to the referencing unit from the determination of the positions of the marker elements of the referencing unit, for example, by comparison with marker element geometries stored in a data base.

Figure 1:
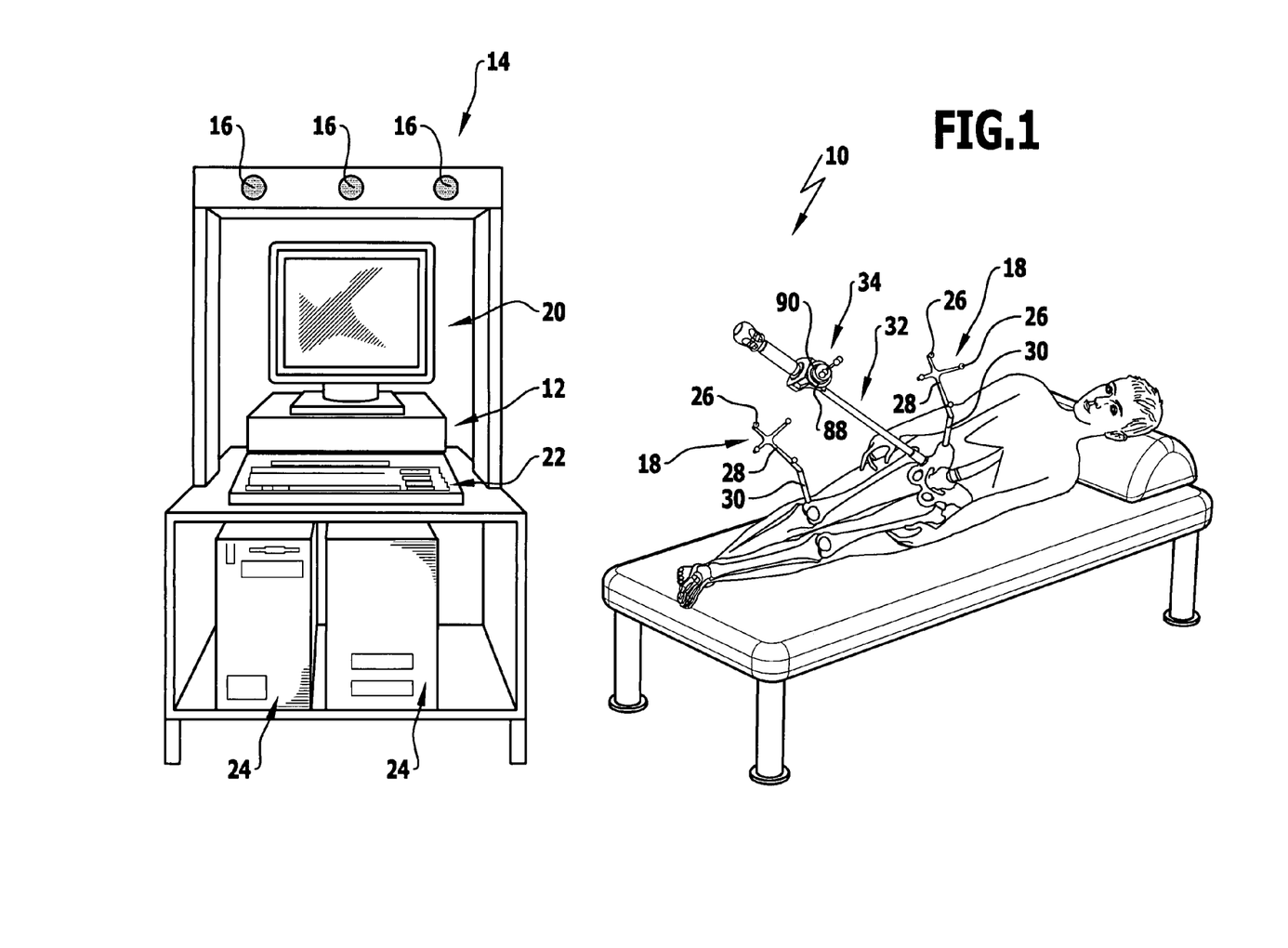
FIG. 1 shows a diagrammatic overall representation of a surgical navigation system.

FIG. 1 shows a surgical navigation system, generally designated by reference numeral 10, which together with all other devices and parts described below forms in its entirety a surgical system. It comprises a transmitting and receiving station 14 controlled by a computer 12 serving as data processing device. The transmitting and receiving station 14 comprises a plurality of transmitting and receiving units 16 for transmitting and receiving electromagnetic radiation, both in the visible and in the infrared range, or ultrasound, which are transmitted or reflected by a reference element 18. The surgical system and/or the navigation system 10 further comprise a display device in the form of a screen 20 and an input device in the form of a keyboard 22. Other computing units 24 may interact with the computer 12 to increase the efficiency of the surgical system or the navigation system 10. In order to ensure that the navigation system 10 will function optimally, two transmitting and receiving units 16 that are spatially separated from each other are preferably provided. There could, however, also be three or more.

The reference element 18 forming a referencing unit, as shown in FIG. 1, is known from the prior art. It comprises at least three passive or active marker elements. Passive marker elements are suited for reflecting or also radiating with delay electromagnetic radiation or ultrasound transmitted by the transmitting and receiving units 16. Active marker elements 26, in contrast, may generate and transmit electromagnetic radiation themselves, alternatively also ultrasound, which can be received by the transmitting and receiving units 16. If only active marker elements 26 are used, it is also possible to provide purely receiving units instead of the transmitting and receiving units 16.

The reference element 18 comprises a cross-shaped support 28, on which the marker elements 26 are immovably held in the form of passive marker elements. The reference elements 18 may be arranged on implants, such as, for example, the bone screws 30 shown in FIG. 1, or on surgical instruments 32.

If the reference elements 18 used in the surgical operation are of identical construction, it is then not possible for the navigation system 10 to automatically differentiate between them. Therefore, prior to performing a surgical operation using the reference elements 18, an initial determination of position is required, which must be carried out manually. To do so, the reference element 18 to be initialized is usually palpated at points provided for this purpose using a calibration instrument, the spatial position and orientation of which is known. As a result of performance of this initialization process, the location and/or orientation information of the calibration instrument is, so to speak, transferred to the reference element 18 or allocated to it.

To determine a position and/or an orientation of, for example, the surgical instrument 32, it is also possible to use a referencing unit 34 in accordance with the invention instead of the reference elements 18. It comprises a base body 36 or support on which at least one marker element 38, in the embodiment shown in FIGS. 1 to 3 a total of 4 marker elements 38, is arranged. It is also conceivable to provide two, three or even five or more marker elements 38. The marker elements 38 are movably mounted on the base body 36. The movable mounting of the marker elements 38 on the base body 36 is, in principle, identical for all marker elements 38 and will be described below, by way of example, for one marker element.

An elongate sleeve 44 is mounted in a bore 42 extending perpendicularly to a flat base area of the substantially cylindrical base body 36. The sleeve 44 comprises an end 46 terminating with the base area 40, and a second end 50 projecting from an approximately hemispherical end face or upper side 48 of the base body 36 that faces away from the base area 40. Over somewhat more than half of its total length, the sleeve 44 projects beyond the upper side 48. An end section 52 directed towards the end 50 defines a longitudinal axis 53 which includes with a longitudinal axis 56 defined by the bore 42 an angle 54 of approximately 35°.

The passive marker element 38 which, in the form of a sphere, is provided on its outer surface with a coating that reflects electromagnetic radiation and/or ultrasound, is attached to a cylindrical guide body 58 which, in an initial position of the referencing unit 58, starting from the end 50, enters the sleeve 44 almost completely.

Figure 4:
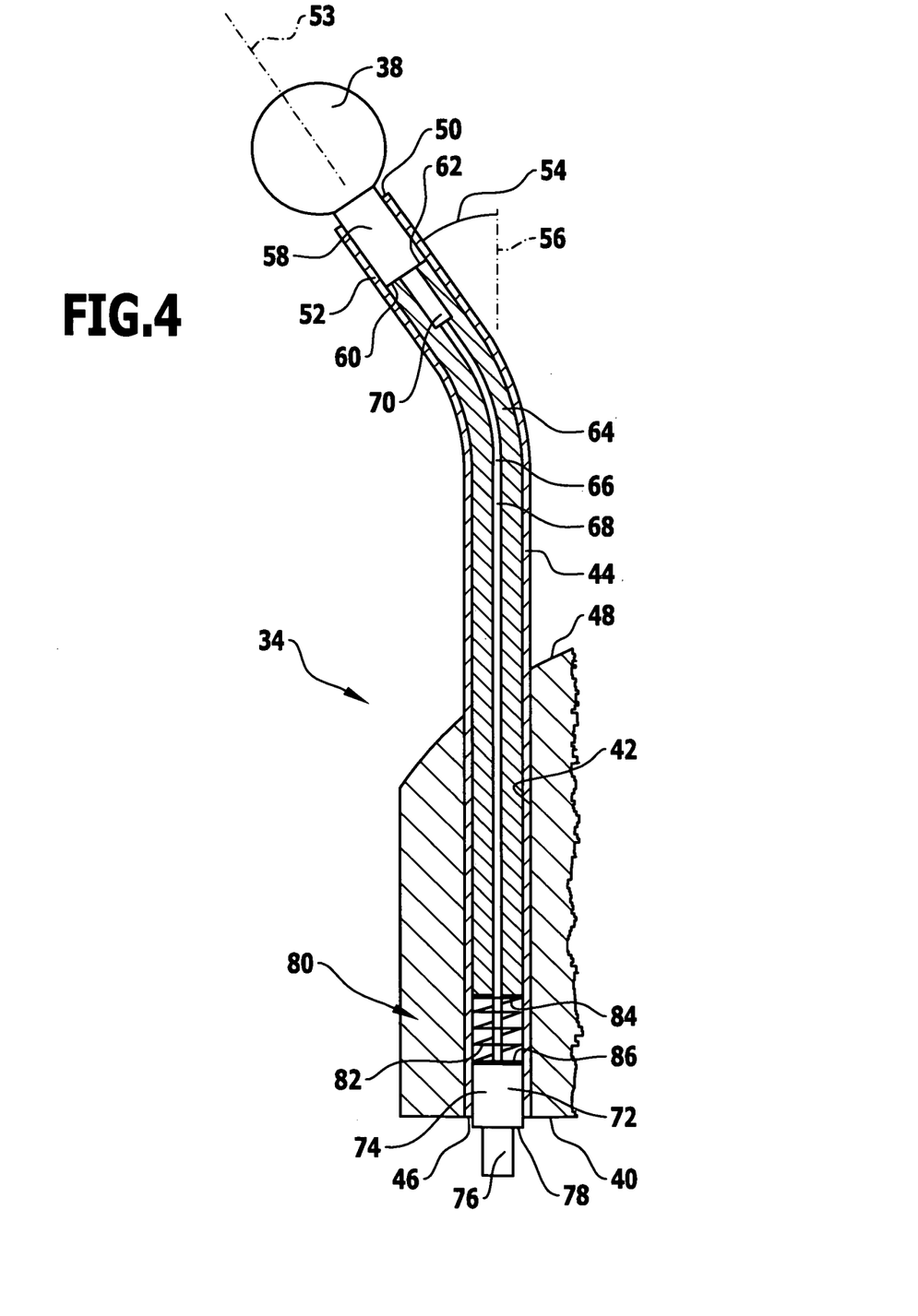
FIG. 4 shows a partially sectional view of a first embodiment of a surgical referencing unit.

In the initial position shown in FIG. 4, a flat face 60 of the guide body 58 that faces into the sleeve 44 lies against a ring-shaped end face 62, facing out of the sleeve 44, of a filling material 64 filling out the inner cross section of the sleeve 44 and extending almost as far as the end 46 of the sleeve 44 inside it. A channel 66 is formed in the filling material 64 for guiding a bar-shaped force transmitting member 68 having a certain elasticity so as to be displaceable in the channel 66 formed coaxially with a center line of the curved sleeve 44. A diameter of the channel 66 is approximately only one sixth of an inner diameter of the sleeve 44.

The force transmitting member 68 is connected at its end facing the end 50 to a cylindrical section 70 of smaller diameter than that of the guide body 58. The other end of the section 70 is immovably fixed to the end face 60.

Figure 2:
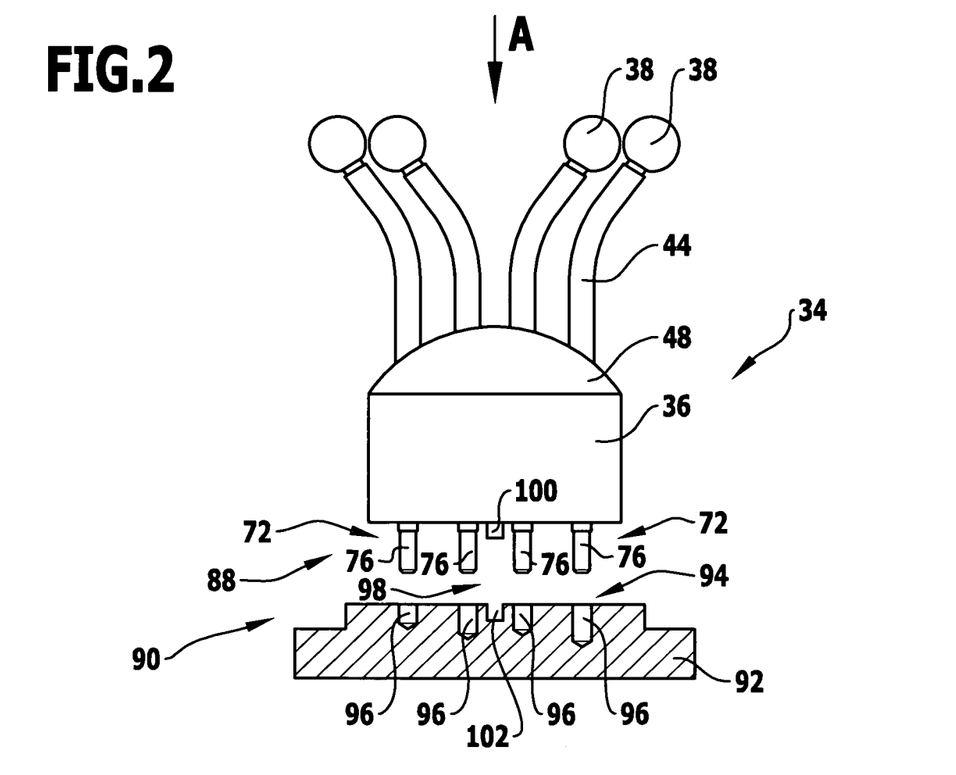
FIG. 2 shows a partially sectional side view of a surgical referencing unit which in FIG. 1 is fixed to an instrument.
Figure 3:
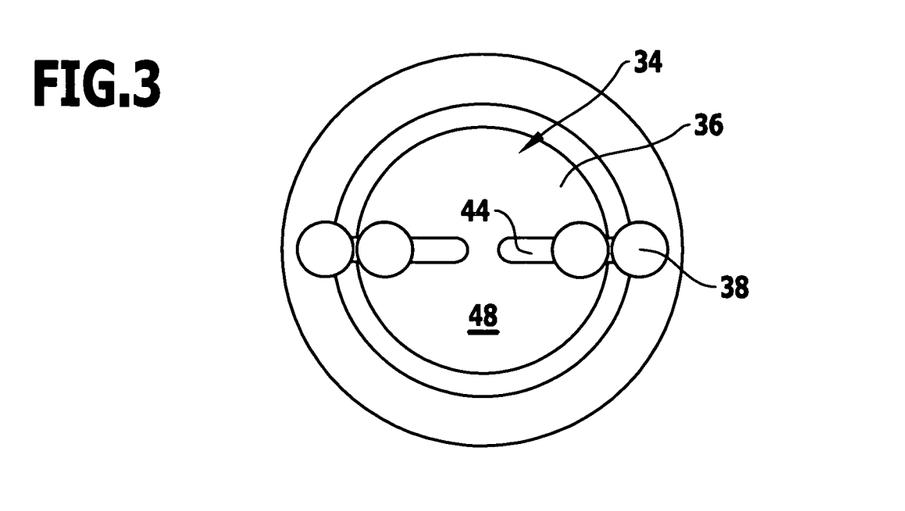
FIG. 3 shows a view of the referencing unit from FIG. 2 in the direction of arrow A.

The end of the force transmitting member 68 facing in the direction towards the end 46 is connected to an interface member 72 which comprises a first cylindrical section 74, the outer diameter of which is adapted to the inner diameter of the sleeve 44 so that the section 74 is displaceably guided in the region of the end 46 of the sleeve 44. The sleeve 44 thus forms at least part of an interface member guiding device. A second cylindrical actuating section 76 is attached coaxially with the section 74 to its end face 78 projecting beyond the base area 40 and extends, in an initial position of the referencing unit 34, as shown in FIG. 2, completely out of the end 46 of the sleeve 44. A part of a resetting member 82 in the form of a helical screw forming a resetting device 80 is supported, on the one hand, on a ring surface 84 of the filling material 64 facing in the direction towards the end 46 and surrounds the force transmitting member 68. The other end of the helical spring is supported on an end face 86 of the section 74, which faces in the direction towards the ring surface 84. The force transmitting member 68 is fixedly connected to the end face 86.

Owing to the described arrangement, the marker element 38 can be moved away from the end 50 and parallel to the longitudinal axis 53 by the actuating section 76 of the interface member 72 being acted upon parallel to the longitudinal axis 56 in the direction towards the filling material 64. The resetting member 82 is thereby compressed, and so movement of the marker element 38 occurs against the action of the resetting device 80. When no force is applied, the resetting member 82 forces the interface member 72 back into the initial position, if it was deflected out of it, and also the marker element 38 connected to the interface member 72 by means of the force transmitting member 68.

The interface members 72 of the referencing unit 34 form altogether a first interface device 88. It makes it possible for all marker elements 38 of the referencing unit 34 to be moved independently of one another and to be brought into different marker element positions. Marker element positions may, in particular, be predefined by a second interface device 90. This may be permanently and fixedly connected to the instrument 32 or an implant 30 or be releasably connectable to these. The releasable connectability makes it possible to equip instruments 32 or implants 30 selectively with different second interface devices 90.

The second interface device 90 comprises a further base body 92 in the form of an essentially flat disc. It comprises in accordance with the number of marker elements 38 on the referencing unit 34 coding elements 94 in the form of blind holes 96 of different depth. The blind holes 96 are so arranged that the interface members 72 can enter a respective blind hole 96. In dependence upon the depth of the blind holes 96, the interface members 72, which, with the actuating section 76, strike a bottom of the coding elements 94, if these are not as deep as a height of the projection formed by the interface member 72, are forced against the action of the resetting device 80 into the sleeve 44, whereby the marker element 38 coupled to the interface member 72 is moved away from the end 50, namely to the extent to which the interface member 72 projects further beyond the base area 40 than the associated blind hole 96 is deep.

Definite marker element geometries, i.e., spatial positions of the marker elements 38 of the referencing unit 34 relative to one another, can thus be defined by corresponding construction of the blind holes 96. If such marker element geometries are stored in a data base of the navigation system 10, it is then conversely possible upon determination of the positions of the marker elements 38 with the navigation system 10 to identify the coding of the second interface device 90. If the second interface device 90 is allocated to a certain instrument 32, then as a result of the interaction of the first and second interface devices 88 and 90, the navigation system 10 can determine not only a spatial position and/or orientation of the referencing unit 34 but, at the same time, also the instrument 32 coded by means of the second interface device 90. An initial calibration of the referencing unit 34, as described above, and allocation to the instrument 32 manually by an operator are, therefore, no longer required.

For safe mechanical connection of the base body 36 to the base body 92, a coupling device 98 may, furthermore, be provided, which comprises at least one first coupling element 100 on the referencing unit 34, for example, on the base body 36, and a second coupling element 102 on the second interface device 90, for example, on the base body 92. The first coupling element 100 and the second coupling element 102 are preferably so constructed that in a connected position of the first and second interface devices 88 and 90, the coupling elements 100 and 102 engage each other with force and/or positive locking. The first coupling element 100 may, for example, take the form of a projection protruding from the base body 36, the second coupling element 102 the form of a recess corresponding in construction to the first coupling element 100, or vice versa.

Figure 5:
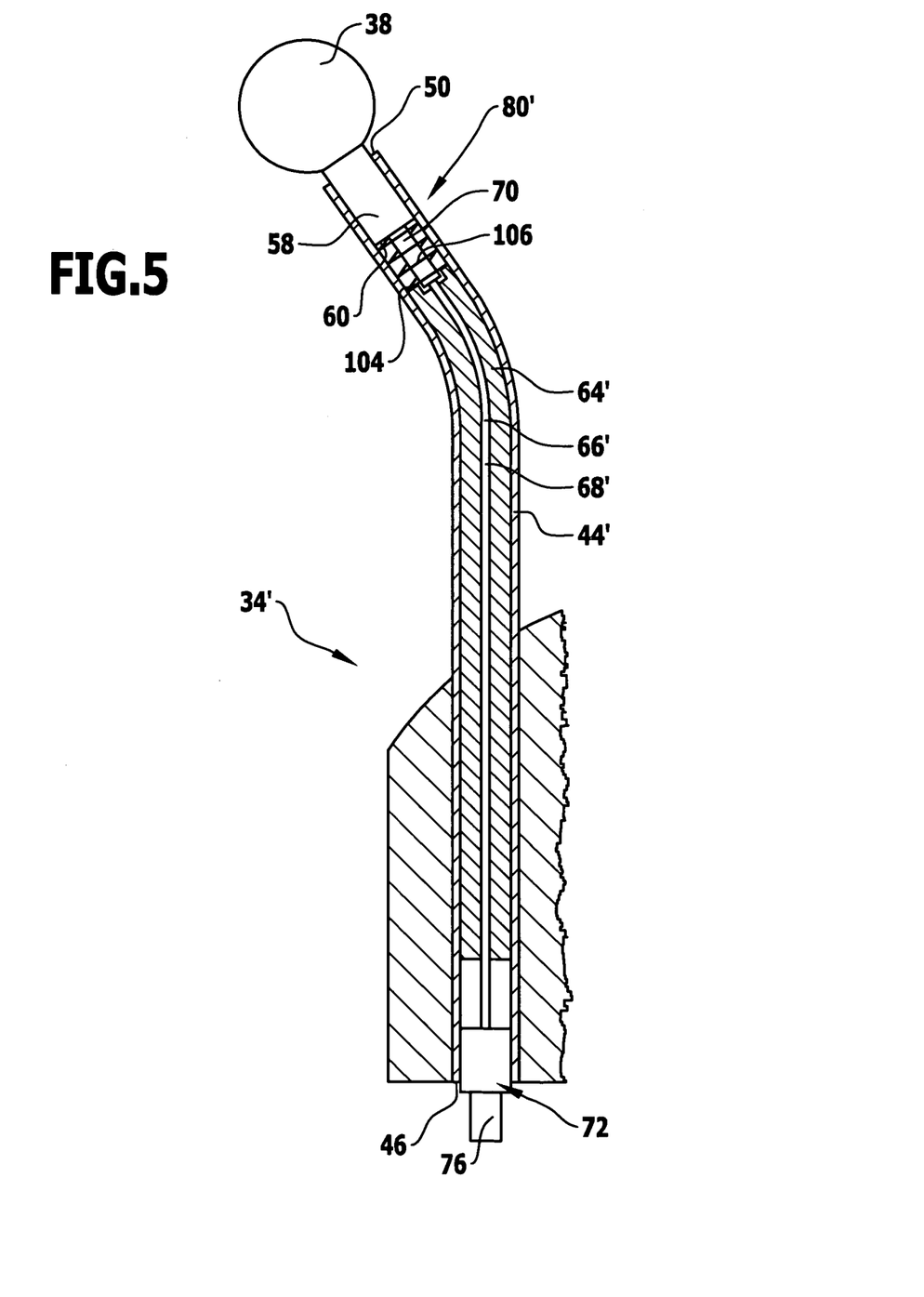
FIG. 5 shows a view corresponding to FIG. 4 of a second embodiment of a surgical referencing unit.

A somewhat modified variant of the force transmitting mechanism for transferring an actuating force from the interface member 72 to the marker element 38 is shown in FIG. 5. Parts of the referencing unit 34' of modified construction that are also provided in the referencing unit 34, as shown in FIG. 4, are given identical reference numerals with a "'", if somewhat modified.

Seated in the sleeve 44', as described above, is a filling material 64', which defines a channel 66' in which a force transmitting member 68 is analogously guided and is connected to an interface member 72 at its end facing the end 46 of the sleeve 44'. The filling material 64' does, however, not extend as far as the end 50 as does the filling material 64 in the referencing unit 34. Instead, a ring-shaped end face 104 surrounding the channel 66' is formed, to which an end of a helical spring 106 forming a resetting member is attached. The other end of the helical spring 106 which surrounds the section 70 is fixedly connected to the end face 60 of the guide body 58.

If the actuating section 76 is pressed in the direction into the sleeve 44', the guide body 58 is pushed with the marker 38 somewhat further out of the end 50 of the sleeve 44. As the free ends of the helical spring 106 are fixedly connected to the filling material 64' or the guide body 58, the helical spring 106, differently than the resetting member 82 in the referencing unit 34, is subjected to tension and not to compression. Nevertheless, the marker element 38 is deflected out of the initial position shown in FIG. 5 against the action of a resetting device 80'. When no more actuating force is applied to the interface member 72, the helical spring 106 contracts again and transfers the marker element 38 back into its initial position.

The invention claimed is:

1. Surgical referencing unit for a surgical navigation system with which at least one of a spatial position and orientation of the referencing unit is determinable, said referencing unit comprising:

a base body, and at least one marker element arranged on the base body, a spatial position of said at least one marker element being determinable by the navigation system, the at least one marker element being movably mounted on the base body, the referencing unit comprising a first interface device which is configured to be brought into engagement with a second interface device provided on a surgical instrument or an implant in a connected position, wherein the engagement of the first interface device and the second interface device mechanically moves the at least one marker element into a predefined marker element position with respect to the base body.

2. Surgical referencing unit in accordance with claim 1, wherein the at least one marker element comprises at least two marker elements.

3. Surgical referencing unit in accordance with claim 1, further comprising a first coupling device which is configured for coupling with a second correspondingly configured coupling device which is provided on the surgical instrument or the implant, for releasably connecting the base body to the instrument or the implant.

4. Surgical referencing unit in accordance with claim 1, further comprising a means for resetting for biasing the at least one marker element into an initial position from a deflected marker element position when the first interface device is not coupled to the second interface device.

5. Surgical referencing unit in accordance with claim 4, wherein the means for resetting comprises at least one resetting member which holds the at least one marker element biased in the initial position.

6. Surgical referencing unit in accordance with claim 4, wherein the at least one marker element is movable out of the initial position against the action of the means for resetting into the deflected marker element position.

7. Surgical referencing unit in accordance with claim 1, wherein the first interface device comprises at least one interface member which is coupled to the at least one marker element and is movably mounted and arranged in such a way that as a result of an actuating force acting on the interface member, the at least one marker element is movable from an initial position, which the at least one marker element assumes when the first interface device is not coupled to the second interface device, into a deflected marker element position.

8. Surgical referencing unit in accordance with claim 7, wherein one of the at least one interface member is associated with a corresponding one of the at least one marker element.

9. Surgical referencing unit in accordance with claim 7, wherein the at least one interface member is mounted for displacement on the first interface device.

10. Surgical referencing unit in accordance with claim 7, wherein the at least one interface member is deflectable from an initial interface member position, against the action of a means for resetting for biasing the at least one interface member into the initial interface member position, into a deflected interface member position when the first interface device is coupled to the second interface device.

11. Surgical referencing unit in accordance with claim 7, wherein the at least one interface member comprises an actuating section which, in the initial position, projects at least partially from the base body.

12. Surgical referencing unit in accordance with claim 7, further comprising an interface member guiding device for guiding movement of the at least one interface member from an initial interface member position into a deflected interface member position and back.

13. Surgical referencing unit in accordance with claim 7, wherein the at least one interface member is coupled to the at least one marker element by a force transmitting member.

14. Surgical referencing unit in accordance with claim 7, wherein at least two of the at least one interface members are movable independently of one another.

15. Surgical instrument, comprising:
a surgical referencing unit for a surgical navigation system, with which navigation system at least one of a spatial position and orientation of the reference unit is determinable,
said referencing unit comprising a base body and at least one marker element arranged on the base body, a spatial position of said at least one marker element being determinable by the navigation system, the at least one marker element being movably mounted on the base body,
the referencing unit comprising a first interface device which is configured to be brought into engagement with a second interface device provided on the surgical instrument in a connected position,
wherein the engagement of the first interface device and the second interface device mechanically moves the at least one marker element into a predefined marker element position with respect to the base body.

16. Surgical instrument in accordance with claim 15, wherein said surgical referencing unit comprises a means for resetting for biasing the at least one marker element into an initial position from a deflected position when the first interface device is not coupled to the second interface device.

17. Surgical instrument in accordance with claim 15, wherein the second interface device comprises at least one coding element which, in interaction with the first interface device, forces the at least one marker element into the predefined marker element position.

18. Surgical instrument in accordance with claim 17, wherein the second interface device comprises at least as many of the coding elements as there are marker elements provided on the referencing unit.

19. Surgical instrument in accordance with claim 17, wherein the second interface device comprises a second base body which carries the at least one coding element.

20. Surgical instrument in accordance with claim 17, wherein the at least one coding element is immovably formed on the second interface device.

21. Surgical instrument in accordance with claim 15, further comprising a second coupling device which is configured for coupling with a first correspondingly configured coupling device which is provided on the referencing unit, for releasable connection of the base body to the surgical instrument.

22. Surgical navigation system, comprising:
at least one referencing unit, and
at least one detecting device for detecting at least one of a spatial position and orientation of the referencing unit,
said referencing unit comprising a base body and at least one marker element arranged on the base body, a spatial position of said at least one marker element being determinable by the navigation system, the at least one marker element being movably mounted on the base body,
the referencing unit comprising a first interface device which is configured for engagement with a second interface device provided on a surgical instrument or an implant in a connected position,
wherein the engagement of the first interface device and the second interface device mechanically moves the at least one marker element into a predefined marker element position with respect to the base body.

23. Surgical navigation system in accordance with claim 22, wherein said surgical referencing unit comprises a means for resetting for biasing the at least one marker element into an initial position from a deflected position when the first interface device is not coupled to the second interface device.

24. Surgical navigation system in accordance with claim 22, further comprising at least one surgical instrument having the second interface device.

25. Surgical navigation system in accordance with claim 24, further comprising two or more instruments, which comprise different, coded second interface devices for different positioning of the at least one marker element of the referencing unit.

* * * * *